United States Patent
Hartmann

(10) Patent No.: US 6,970,729 B2
(45) Date of Patent: Nov. 29, 2005

(54) METHOD AND DEVICE FOR DETERMINING LOCAL DISTRIBUTION OF A MEASURING PARAMETER

(75) Inventor: Paul Hartmann, Weiz (AT)

(73) Assignee: Perimed AB, Järfälla (SE)

( * ) Notice: Subject to any disclaimer, the term of this patent is extended or adjusted under 35 U.S.C. 154(b) by 0 days.

(21) Appl. No.: 10/149,383

(22) PCT Filed: Nov. 30, 2000

(86) PCT No.: PCT/AT00/00321

§ 371 (c)(1),
(2), (4) Date: Jun. 25, 2002

(87) PCT Pub. No.: WO01/43628

PCT Pub. Date: Jun. 21, 2001

(65) Prior Publication Data

US 2003/0050543 A1    Mar. 13, 2003

(30) Foreign Application Priority Data

Dec. 14, 1999 (AT) ..................................... 2106/99

(51) Int. Cl.$^7$ .............................................. A61B 5/00
(52) U.S. Cl. ........................................ 600/317; 600/322
(58) Field of Search ........................... 600/309–310, 600/322, 317

(56) References Cited

U.S. PATENT DOCUMENTS

| | | | |
|---|---|---|---|
| 4,476,875 A | | 10/1984 | Nilsson et al. |
| 4,862,894 A | | 9/1989 | Fujii |
| 5,361,769 A | | 11/1994 | Nilsson |
| 5,376,336 A | * | 12/1994 | Lubbers et al. ............. 600/310 |
| 5,485,530 A | | 1/1996 | Lakowicz et al. |
| 5,593,899 A | * | 1/1997 | Wilson et al. ............... 436/127 |
| 5,830,132 A | * | 11/1998 | Robinson ..................... 600/310 |
| 5,830,133 A | * | 11/1998 | Osten et al. ................. 600/322 |
| 5,978,691 A | * | 11/1999 | Mills ........................... 600/334 |
| 5,983,120 A | * | 11/1999 | Groner et al. ............... 600/310 |
| 6,006,128 A | * | 12/1999 | Izatt et al. ................... 600/476 |
| 6,064,898 A | * | 5/2000 | Aldrich ....................... 600/316 |
| 6,263,227 B1 | * | 7/2001 | Boggett et al. ............. 600/473 |

FOREIGN PATENT DOCUMENTS

| | | |
|---|---|---|
| EP | 0354204 | 2/1990 |
| EP | 0516610 | 6/1995 |
| GB | 2033575 | 5/1980 |

OTHER PUBLICATIONS

P. Hartmann et al., "Fluorescence Lifetime Imaging of the Skin $PO_2$ Supply" in Oxygen Transport to Tissue XIX, New York, 1997, pp. 605-611.

* cited by examiner

Primary Examiner—Eric F. Winakur
Assistant Examiner—Matthew Kremer
(74) Attorney, Agent, or Firm—Dykema Gossett PLLC

(57) ABSTRACT

A system and method for determining the local distribution of measurement variables being measured relative to or present in a predefined measurement area of a biological sample wherein in a first optical measuring process the local distribution of a first of the measurement variables is determined using a sensor film applied to the measurement area and including a luminescence indicator reacting to the first measurement variable by a change of luminescence decay time. The luminescence decay time or a quantity derived therefrom is recorded by an imaging technique as a function of the first measurement variable. In a second optical measuring process the local distribution of a second of the measurement variables is determined simultaneously or immediately following, using an imaging technique which is effective through the sensor film of the first optical measuring process.

15 Claims, 3 Drawing Sheets

METHOD AND DEVICE FOR DETERMINING LOCAL DISTRIBUTION OF A MEASURING PARAMETER

BACKGROUND OF THE INVENTION

1. Field of the Invention

The invention relates to a method for determining the local distribution of a quantity to be measured relative to or present in a predefined measurement area of a biological sample, preferably the surface of an organ or the epidermis, where in a first measuring process for determining a first measurement variable a sensor film with a luminescence indicator reacting to this variable by a change of at least one optical characteristic is applied to the measurement area and the first measurement variable is detected by imaging means, as well as to a system for implementation of this method.

2. The Prior Art

For a variety of medical applications, especially in the diagnostic sector, it is of prime importance that the local distribution of a measurement variable over the surface of an organ, such as the human skin, or the distribution of the flow rate of a given substance through an interface, should be determined. Besides, such measured results are useful in checking and controlling methods of medical therapy.

Tissue oxygenation, for example, is an important parameter in diagnosing diseases resulting from disturbed microcirculation. Oxygen supply is determined on the one hand by the perfusion properties of the blood, and on the other hand by transcutaneous transport properties and oxygen consumption in the skin. In addition, oxygen supply is partly effected by oxygen absorption from the environment, an activity known as cutaneous respiration. Problems occur when several parameters influencing the medically relevant variable to different degrees, are to be detected simultaneously.

Determining oxygen concentration or transcutaneous oxygen partial pressure ($tcPO_2$) by means of skin electrodes is a technique well known in the art, as is the use of optical sensors based on fluorescence quenching. The latter do not consume oxygen during measuring, which is an advantage over the use of electrodes.

Another known technique is the so-called FLIM (fluorescence lifetime imaging) process using optical sensors on the basis of fluorescence quenching, where a sensor membrane carrying a suitable luminescence indicator is attached to the skin region to be examined. Oxygen diffused through the skin surface enters the sensor membrane, and fluorescence quenching resulting therefrom may be analyzed by the detector system.

In this context apparatus and method for measuring tissue oxygenation are described in U.S. Pat. No. 5,593,899, where oxygen-dependent quenching of a fluorescence indicator is used for measurement. The oxygen supply of the skin is determined by applying a luminescent probe within a skin cream to a suitable area of the skin, and covering that area by an oxygen-impermeable film. The optical means for excitation of the indicator and detection of the respective radiation is encased in a housing whose transparent cover is directly placed over the $O_2$-impermeable film. An interference filter and a photodiode are added to this set-up. The luminescent probe is subject to excitation radiation from a modulated radiation source via optical fiber guides. The above set-up is suitable only for integral measuring over the entire area covered by the optical equipment. It is impossible with this system, however, to obtain accurate information on boundary regions between sufficiently oxygenated and inadequately oxygenated skin regions.

The device disclosed in EP 0 516 610 B1 can be used for measuring not only oxygen concentration, but also oxygen flow through an interface, for example, a skin area. The sensor layer of the device to be associated with the interface offers a known, finite resistance to the oxygen flow to be measured, and is provided with at least one optical indicator determining oxygen concentration on one side of the sensor layer. From the concentration value measured on one side of the sensor layer and known beforehand on the other side (ambient air) the material flow through the interface is determined. According to a variant of the invention the sensor layer may be scanned a really by means of an imaging system (CCD), so that local distribution of oxygen flow or oxygen concentration may be measured.

Further ideas and measured results regarding local distribution of oxygen flow and subcutaneous oxygen concentration, as well as a proposal for a measuring process by imaging means are disclosed in the paper "Fluorescence Lifetime Imaging of the Skin $PO_2$: Instrumentation and Results" in Advances in Experimental Medicine and Biology, Vol. 428, pp 605–611 (1997), published by Plenum Press N.Y. The paper describes a sensor membrane for measuring transcutaneous oxygen concentration, which comprises an optical insulating layer facing the skin surface, a sensing layer with a luminescence indicator with $O_2$-sensitive decay time, and a supporting layer that is impermeable to oxygen. Further described is a membrane for measuring oxygen flow, which differs from the above sensor membrane by featuring a diffusion barrier with known oxygen permeability instead of the $O_2$-impermeable layer. For the purpose of measurement the sensor membrane is applied to the measuring surface, for example, a skin area. The measuring process employs a modulation technique, where the LEDs emitting excitation radiation in the direction of the sensor membrane are actuated by a square-wave generator and emit square-wave modulated excitation radiation. The emission radiation emitted by the sensor membrane is detected by a CCD camera with modulated amplification and passed on pixel by pixel to a computing unit for image-processing. The oxygen distribution measured in a polymeric layer is documented as an image of the variations in oxygen distribution over an area of the skin.

Other imaging processes for measurement by means of phase fluorometry are described in U.S. Pat. No. 5,485,530.

A complete estimate of the oxygen supply of a certain area of the skin or surface of an organ can only be made if the oxygen status of the inspected region is complemented by information on blood supply and perfusion rate.

A number of well-advanced methods and devices are at disposal for obtaining the necessary information on perfusion, such as Laser-Doppler flow measurements (see U.S. Pat. No. 4,476,875), by means of which local perfusion of the blood vessels may be examined on the basis of the frequency shift of radiation emitted by a laser lightsource. It would also be possible to expand emission radiation by suitable optical means, or measurement areas could be scanned step by step with the use of a laser beam, so that a picture will be obtained of the local distribution of the perfusion rate. Such methods have become known as Laser-Doppler imaging processes (LDI). The result of a Laser-Doppler measurement will depend on the velocity and number of red blood cells scattering the laser light.

In U.S. Pat. No. 4,862,894, for example, a system for analyzing the bloodstream in an area of the skin is described, where a laser beam is used which is expanded by a cylindrical lens. In one variant the skin surface is scanned by the laser line by line, and a two-dimensional image is detected of how the flow velocity of the blood is distributed. Another method and apparatus for measuring fluids in motion is described in U.S. Pat. No. 5,361,769, where the area of a specimen is scanned by a Laser-Doppler imaging process. Via a lens combination in the laser beam varying object distances are compensated, thus increasing measuring accuracy.

So far it has not been possible to obtain satisfactory measured results on the oxygen supply of an organ or a skin area as the quantities to be measured usually vary at a rate that is faster than the rate at which the different measuring devices or processes required therefor can be successively employed in the skin area to be analyzed. A further problem is presented by the heterogeneity of the area to be measured, e.g., the surface of the skin, so that point measurements such as electrode or Laser-Doppler flow measurements are not successful whilst imaging systems and processes such as FLIM and LDI can only be used in adjacent sites or one after the other. For example, when tests on one and the same skin area switch from an FLIM to LDI system, this will take too long for parameters like perfusion and oxygen status, which frequently change within seconds, thus preventing meaningful measurement. When devices have to be exchanged, it will be difficult to reposition them precisely, so that measured areas are likely to vary slightly.

Using previous measuring systems as a basis, it is the object of this invention to propose a method and apparatus for determining local distribution of several measurement variables in a predefined measurement area of a biological sample, which should enable the user to obtain information on physiological parameters and their localization.

SUMMARY OF THE INVENTION

According to the invention this object is achieved by providing that for simultaneous or immediately following determination of the local distribution of at least one further variable in the same measurement area a second optical measuring process is employed which is effective through the sensor film.

A system in accordance with the invention for implementation of the method is characterized by a second optical measuring device for whose excitation and emission radiation the sensor film of the first optical measuring device is transparent, so that two independent optical measuring means will cover the same measurement area. The two measurements may be taken simultaneously or in such rapid succession that the physiological parameters will remain largely unchanged in this short time period.

An essential feature of the invention is that the local distribution of at least two parameters or measurement variables of a biological sample is determined by two independent optical measuring processes or systems, in order to improve diagnostic findings. One measuring process is based on luminescence-optical determination of a parameter using a sensor membrane with a luminescence indicator incorporated therein, while for the second or further simultaneous, optical measuring processes the sensor membrane or sensor film must be sufficiently transparent to permit optical measurement with satisfactory signal yield.

Advantageously, a luminescence-optical method should be used as first measuring process, in which luminescence decay time or a quantity derived therefrom as a function of a first measurement variable is recorded by an imaging technique. The main advantage of determining decay time is that the measurement will become independent of the local light intensity of the sensor film. This will permit full lighting even of strongly curved surfaces of the skin or some other organ by means of a simple lighting set-up without the need for homogeneous excitation of the luminescent indicator. Care should be taken, however, that sufficient luminescence be provided in each area of the sensor membrane for decay time measurement. Since decay time measurement does not depend on object distance, and the propagation time of the light from object surfaces at varying distances is negligible, decay time may be determined with sufficient accuracy for measurement surfaces of any curvature. Thus a major demand will be fulfilled with regard to trouble-free and safe measuring of the arms and legs or other curved skin areas of a patient. When a luminescence signal is detected a special CCD camera is operated such that the information contained in every pixel may be brought into relationship with the decay time at the respective measurement site corresponding to the pixel. Alternatively, a CMOS sensor may be used instead of the CCD camera.

As first quantity to be measured local distribution of oxygen concentration ($tcPO_2$), and preferably transcutaneous oxygen concentration, or local distribution of oxygen flow ($O_2$-flux) through the organ surface, preferably the skin surface, may be determined.

It would also be possible to determine local distribution of $CO_2$ concentration or $CO_2$ flow as first measurement variable.

If suitable luminophores are used the luminescence-optical measuring process is well suited for determining local distributions of temperature, glucose concentration, or an ionic concentration, such as the pH level.

As a second measuring process a Laser Doppler imaging process (LDI process) may be used by means of which the perfusion rate in the measurement area is determined. To obtain strong temporal and local correlation for perfusion rate and oxygen status of a biological sample, both measurements must be taken practically simultaneously within one and the same sample area. The high local resolution of modern LDI systems (<100 $\mu$m) can be well combined with a fluorescence lifetime imaging (FLIM) technique, thus giving excellent diagnostic results.

The properties of the measurement process will be discussed in more detail below, with reference to a typical application, i.e., oxygen supply of the human skin. It is to be appreciated that this will put no restriction on the overall scope of the invention.

A major advantage of the invention is that both local oxygen concentration (first parameter) in the sensor film (and thus in the biological sample of interest) and perfusion in the same area (second parameter) are determined, recorded by imaging and assessed by comparison, with strong temporal and local correlation in an extended measurement area. As the local oxygen concentration in the indicator layer of the sensor film is known, $O_2$ partial pressure at the skin surface or $O_2$-flux may be computed in dependence of $O_2$ diffusion properties of the supporting membrane and allowing for barometric pressure. From the local perfusion measured in the skin area under inspection the blood supply of the tissue beneath the sensor membrane may, be inferred, the high resolution of the local and temporal correlation between perfusion and $tcPO_2$ or $O_2$-flux offering a comprehensive picture of the decisive parameters (perfusion and oxygen concentration). Combination of these parameters will permit a new quality of medical diagnosis, which to date has been limited by the separate use of the methods described as a combined process above, or other, previous measurement processes.

In a variant of the invention a photometric or photographic method may be used as a second or further measuring process, where the measurement area is recorded as an image in a predefined range of wavelengths. In this way autofluorescence or infrared radiation may be imaged in the measured area. By means of infrared photography local heat distribution of a skin area may be detected as additional information.

Whereas in conventional luminescence-optical processes an optically isolating layer is usually applied between the skin and the sensor membrane for optical decoupling of emission radiation and background fluorescence, the present invention features the use of a transparent sensor film, so that other measures must be taken to exclude stray light components during measurement. One possibility would be to detect luminophores with a long decay time (e.g., phosphorescent porphyrins or transition metal complexes), once the short-lived luminescence of interfering substances (e.g., melanine, haemoglobin) in the sample has been quenched. For signal separation it would also be possible to use various phase techniques, however.

It is provided in a further variant that a profilometric or interferometric method be employed as a second or further measuring process. This will permit the topography of an organ or skin area to be included in the measurement in addition to the first measured value. Detecting the three-dimensional structure of the measured area is of some bearing for diagnosis and therapy, especially in the field of dermatology or plastic surgery. Besides interferometric methods a stripe projection method may be used, where a parallel ruled grating is projected on the surface to be measured and evaluated by means of a CCD camera placed at a certain angle relative to the projection plane. Small differences in height of the inspected profile produce a distortion of the striped pattern which can be evaluated quantitatively.

The measured area could also be assessed visually through the sensor film (for example, by processes of epiluminescence microscopy). If a transparent sensor film is used the measured area may be assessed by visual inspection, and morphological changes, such as colour changes or tumor growths may be directly correlated to luminescence data of the first measuring process. It would further be possible to put markings on the skin surface which could be recorded visually or photographically through the transparent sensor film.

In further development of the invention it is provided that errors in the measured results of the second optical measuring process, which are due to the sensor film, be corrected by a computing procedure or suitable calibrating parameters. Radiation emitted by the LDI unit is subject to slight attenuation and scattering as it passes through the sensor film. If the entrance vector of the LDI beam is not normal to the boundary surface of the sensor film (due to the curved surface of the measured object), a slight lateral displacement of the radiation path will result, which may be neglected on account of the low thickness of the sensor film of about 50 $\mu$m. On the other hand a certain part of the radiation will also be scattered during its passage from the skin through the sensor film to the LDI detector. As a consequence, the measured value will further deviate from the value that would be obtained if no sensor film were present. By means of suitable corrections using a computing procedure or stored calibration values it will be possible to largely eliminate the influence of the sensor film.

LDP measurements often take several minutes for complete scanning of the measurement area, depending on the desired resolution. This will also limit temporal resolution of the overall system. FLIM measurements need considerably less time (split seconds). To obtain a correlation of LDI and FLIM images of one and the same measurement area that is satisfactory from the aspect of time, every LDI measurement may be preceded and followed by a FLIM measurement.

As an alternative, LDI and FLIM measurements could be "interlocked", either by a short interruption of the LDI scan and fitting in a split-second FLIM measurement, or by using the short time needed for repositioning the laser beam onto a new measuring point, for performing a FLIM measurement. The lightsources for LDI and FLIM measurements may be operated alternatingly, since the radiation detectors may be made sensitive to the emission radiation of both measurement processes.

In principle it will be possible to perform LDI and FLIM measurements simultaneously. In this case separation of the detected signals must be ensured. This is achieved either by spectral differentiation between LDI signal and luminescence signal and corresponding selection of filters, or by selective electronic filtering of unmodulated and high-frequency modulated signals.

The invention will be explained in more detail bellow, with reference to the schematical drawings enclosed.

DETAILED DESCRIPTION OF THE PREFERRED EMBODIMENTS

Figure 1:
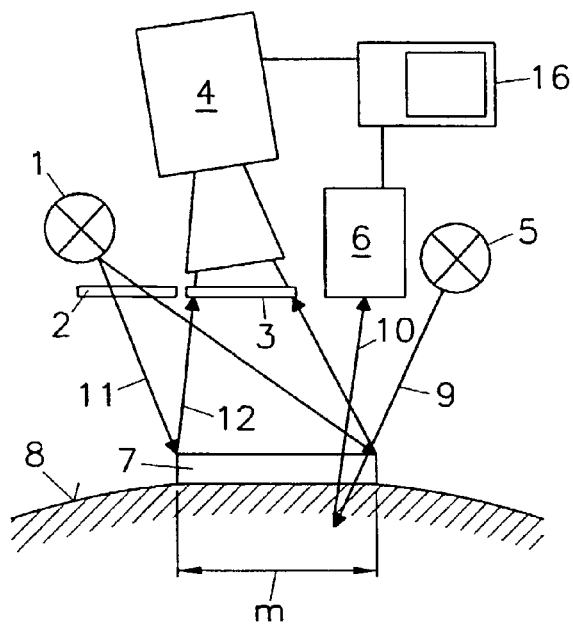
FIG. 1 shows a first variant of a system in accordance with the invention,
FIG. 2 a detail of the system shown in FIG. 1,
FIG. 3 a very simple design variant, and
FIGS. 4 to 9 other advantageous variants of the invention.
Figure 2:
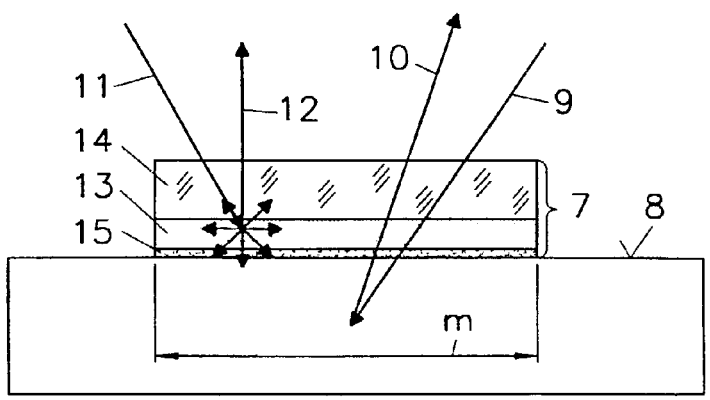

FIGS. 1 and 2 give a schematic view of a first variant of the system proposed by the invention (a combination of FLIM and LDI), which can be used for simultaneously determining oxygen concentration and perfusion rate for a given measurement area m with high local resolution. The exemplary measuring system essentially comprises a transducer (sensor film 7), a fluorescence lifetime imaging unit (FLIM), and a Laser-Doppler imaging unit (LDI).

1. Sensor film: The sensor film 7 shown in FIG. 2 has a transparent support 14 as well as an indicator layer 13 on the side facing the skin surface 8. The indicator layer 13 contains a luminescence indicator, whose fluorescence quenching is uniquely defined by local $O_2$ concentration. The indicator layer 13 should exhibit a sufficient degree of absorption of the excitation radiation 11 emitted by the FLIM unit, whereas the entire sensor film 7 including the support 14 is largely transparent to excitation and emission radiation 9, 10 of the LDI unit 5, 6. Between the skin surface 8 and the indicator layer 13 an adhesive layer 15 may be provided.

A typical variant of the sensor film features a flexible and transparent polymeric multi-layer system, starting with a support 14, for example of polyester, polyethylene, cycloolefin copolymer, or a fluoropolymer, and a flexible indicator layer 13 that is essentially transparent to the emission radiation of the additional measuring process. The indicator layer 13 contains a, possibly oxygen-sensitive, luminscent dye, such as a ruthenium-diimine-complex, an osmium-diimine complex, a platinum porphyrin or palladium porphyrin, which is immobilized in a polymeric matrix, e.g., silicone (with or without silica gel fillers), polyvinyl chloride (PVC) with plasticizer, polymethacrylate (PMMA), or polystyrene (PS).

According to another variant sensors for pH or $CO_2$ levels in the skin may be used, which are based on other indicators, such as hexapyrene-trisulphonic acid, or naphthalimide.

A third polymeric layer of the multi-layer system, which acts as boundary between the sensor and the epidermis, preferably is designed as adhesive layer 15, thus permitting continuous contact with the skin surface and perfect gas diffusion between skin and sensor. This adhesive layer may consist of a mixture of silicone resin and uncured silicones (pressure-sensitive adhesive, PSA).

Figure 6:
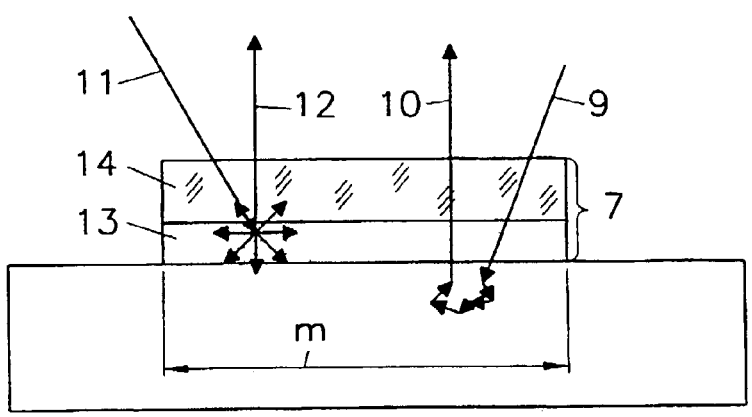
Figure 9:
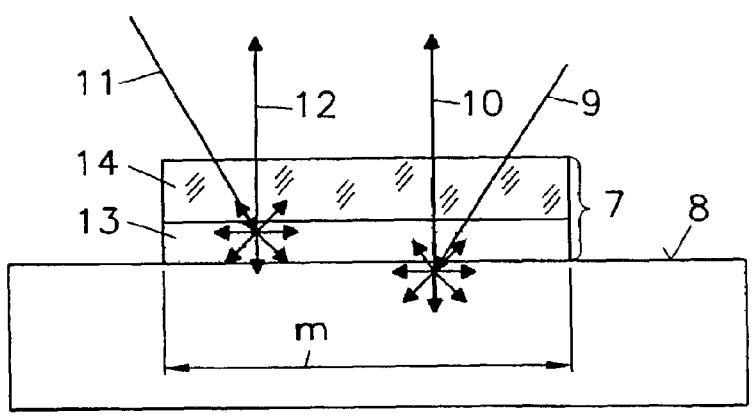

In a variant as shown in FIG. 6 or 9 the matrix immobilizing the dyes could be designed as adhesive layer itself, for example, by incorporating a PSA into the matrix, or employing the PSA itself as matrix for the dye.

2. FLIM unit: This unit includes all mechanical, electronic and optical components necessary for reproducible areawise excitation of the indicator layer 13 and site-selective areawise detection of the radiation 12 emitted by the indicator layer 13. As excitation lightsource 1 a blue light-emitting diode may be used, which applies the excitation radiation 11 via an excitation filter 2 on the sensor film 7. The excitation radiation 11 must be able to pass the essentially transparent support 14 while it should be, at least partially, absorbed by the indicator layer 13 of the sensor film 7. The luminescence radiation 12 coming from the indicator layer 13 is detected via an emission filter 3 by a detection unit 4, preferably a special CCD camera.

The spectroscopic data of an oxygen measurement are given as an example, where the indicator (ruthenium-diimine complexes) is excited by a lightsource (blue LED), the light of which is partly absorbed by the indicator. The absorption maximum of the indicator is situated at wavelengths of 460–490 nm. The emission maximum of the indicator is between 580 and 630 nm. Maximum optical density of the indicator layer in the wavelength range of 430–480 nm is between 0.05 and 0.5.

3. LDI-unit: This unit includes all mechanical, electronic and optical components necessary for scanning the measurement area m covered by the sensor film 7 with excitation radiation 9 through the sensor film 7, and for detecting and analyzing emission radiation 10, and possibly correcting the measured values with regard to scattering characteristics of the sensor film 7. A laser 5 supplies monochromatic radiation of a wavelength that will practically not be subject to absorption by the sensor film 7. Excitation radiation 9 will thus be maintained virtually unattenuated for analysis of the biological sample, for example, the epidermis 8. Emission radiation 10, which is backscattered or reflected by the biologial sample 8, will contain information that can be received and evaluated by the detector 6 of the LDI unit. FLIM and LDI unit have a common input and evaluation unit 16.

In all other variants components of the same kind or function have the same reference numerals.

Figure 3:
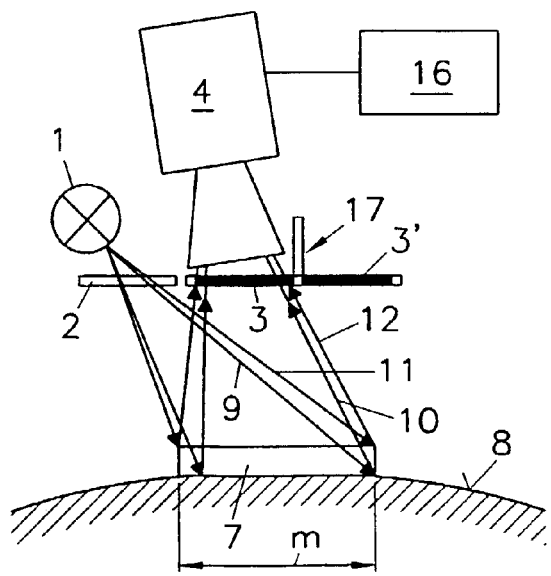

In FIG. 3 a very compact variant of the invention is shown, in which the second optical measuring device is provided with a unit 17 for separation of radiations 10, 12 emitted by the two optical measuring devices, such as a filter wheel with different emission filters 3, 3' for the two radiations 10, 12. The system has only one lightsource 1 and one CCD camera. This variant is particularly well suited if the FLIM process is combined with reflexion spectrophotometry or auto-fluorescence measurement.

Figure 4:
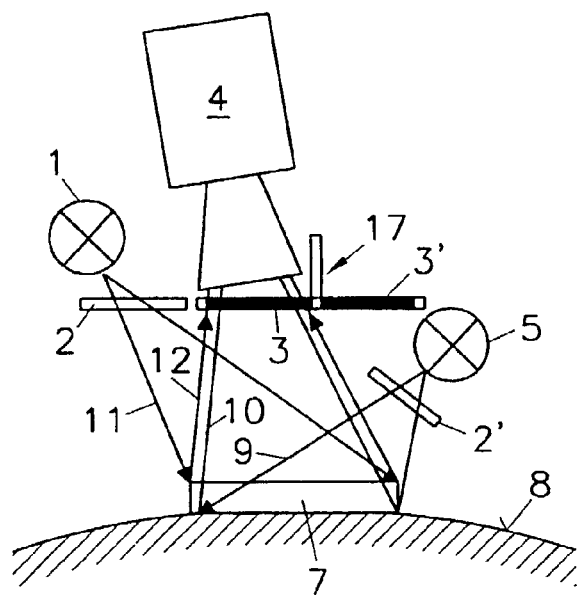
Figure 5:
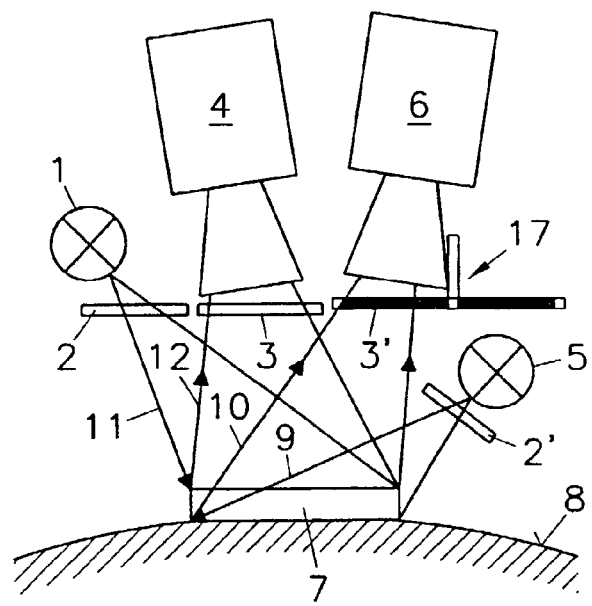

FIGS. 4 to 6 show systems where the FLIM process is combined with reflexion-spectrophotometry. In FIG. 4 a broad-band lightsource is used as separate excitation lightsource 5, whose excitation radiation 9 is directed onto the sample 8 via an excitation filter 2'. For the purpose of measurement the CCD camera 4 of the FLIM process is used, which is fed with the two emission radiations 10, 12 via emission filters 3, 3' of the filter wheel 17. The variant of FIG. 5 differs from that of FIG. 4 by the use of a separate imaging detection unit 6 (such as a second CCD camera), which is supplied with the emission radiation 10 of reflexion spectrophotometry. FIG. 6 shows the interaction between excitation radiation 11 (FLIM) and indicator layer 13, and the scattering of excitation radiation 9 in the epidermis 8.

Figure 7:
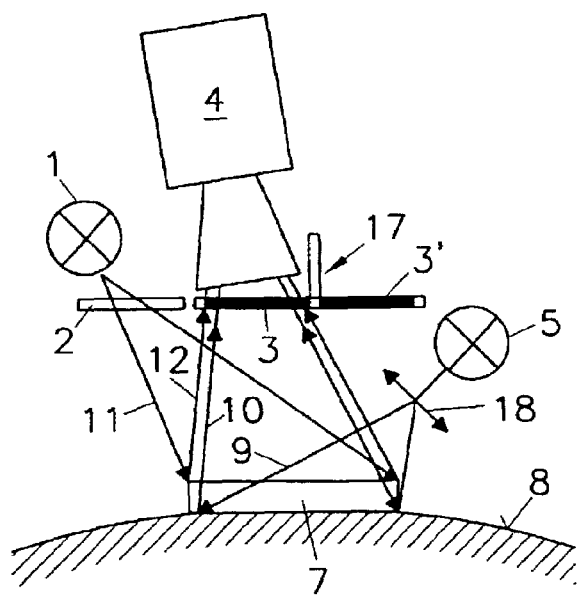
Figure 8:
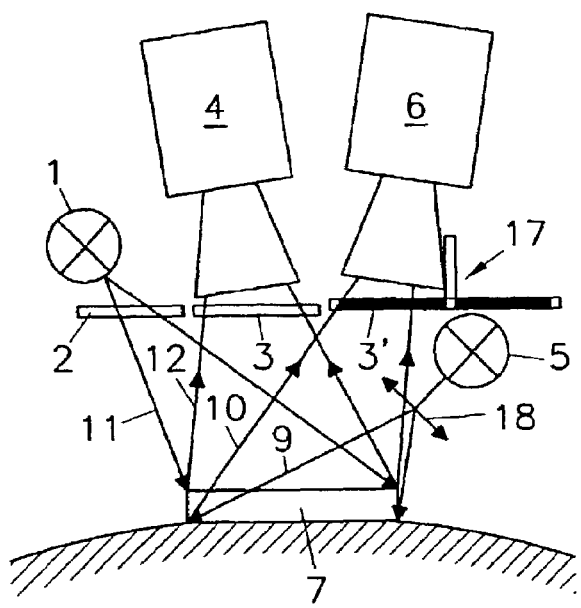

FIGS. 7 to 9 show systems where the FLIM process is combined with autofluorometry. According to FIG. 7 a laser is used as separate excitation lightsource 5, whose light is directed onto the sample 8 by means of a beam expander. Emission radiation 10 may be detected via a filter wheel 17 by the CCD camera 4 (FIG. 7), or by a separate, imaging detection unit 6 (FIG. 8). FIG. 9 shows the interaction between excitation radiation 11 (FLIM) and indicator layer 13, and that of excitation radiation 9 (autofluorescence) in the epidermis 8.

What is claimed is:

1. Method for determining by imaging techniques the local distribution of first and second independent measurement variables measured relative to or present in a predefined measurement area of a biological sample comprising the steps of:

applying a single sensor film to the predefined measurement area of the biological sample, said single sensor film containing a luminescence indicator which reacts to said first independent measurement variable by a change in luminescence decay time, directing first excitation radiation into said single sensor film to excite said luminescence indicator and cause said luminescence indicator to emit first measurement radiation, detecting said first measurement radiation and determining therefrom local distribution of said first independent measurement variable in a first optical measuring process, directing second excitation radiation into and through said single sensor film and into said biological sample to cause second measurement radiation to be emitted from said biological sample, and detecting said second measurement radiation and determining therefrom local distribution of said second independent measurement variable in a second optical measuring process.

2. Method according to claim 1, wherein said biological sample is the epidermis or the surface of an organ.

3. Method according to claim 1, wherein said first measurement variable to be determined is one of the group consisting of the local distribution of oxygen concentration ($tcPO_2$), the local distribution of transcutaneous oxygen concentration and the local distribution of oxygen flow ($O_2$-flux) through an organ surface.

4. Method according to claim 3, wherein said organ surface is skin.

5. Method according to claim 1, wherein said first measurement variable determined is the local distribution of $CO_2$ concentration or the local distribution of $CO_2$ flow.

6. Method according to claim 1, wherein said first measurement variable determined is the local distribution of one of the group consisting of temperature, glucose concentration and an ionic concentration.

7. Method according to claim 6, wherein said ionic concentration is the pH level.

8. Method according to claim 1, wherein said second measuring process is a Laser Doppler imaging (LDI) process being used to determine a perfusion rate in said measurement area as said second measurement variable.

9. Method according to claim 1, wherein said second measuring process is a photometric or photographic method and said measurement area is recorded as an image in a predefined range of wavelengths.

10. Method according to claim 9, wherein autofluorescence in said measurement area is recorded as said image.

11. Method according to claim 9, wherein infrared radiation in said measurement area is recorded as said image.

12. Method according to claim 1, wherein said second measuring process is a profilometric method.

13. Method according to claim 12, wherein said profilometric method is an interferometric method.

14. Method according to claim 1, wherein said second measuring process is a visual inspection of said measurement area being assessed through said sensor film.

15. Method according to claim 1, wherein errors in measured results of said second optical measuring process, which are due to said sensor film, are corrected by a computing procedure or suitable calibrating parameters.

* * * * *